United States Patent [19]

Tsai et al.

[11] Patent Number: 5,723,307
[45] Date of Patent: Mar. 3, 1998

[54] FLUOROGENIC SUBSTRATES FOR ASSAY OF ANGIOTENSIN CONVERTING ENZYME

[75] Inventors: Hsin Tsai; Hui-Ling Chen, both of Taipei, Taiwan

[73] Assignee: Development Center for Biotechnology, Taipei, Taiwan

[21] Appl. No.: 520,770

[22] Filed: Aug. 30, 1995

[51] Int. Cl.$^6$ .............. C12Q 1/37; C12Q 1/00; G01N 33/53; A61K 38/00
[52] U.S. Cl. .................. 435/24; 435/23; 435/4; 435/968; 530/316; 530/300; 530/330; 562/89
[58] Field of Search ............... 435/24, 23, 4, 435/968; 530/316, 300, 330; 562/89

[56] References Cited

PUBLICATIONS

Persson, Anders and Wilson, Irwin B. "A Fluorogenic Substrate for Angiotensin–Converting Enzyme." *Anal. Biochem.* 83, 296–303 (1977) Month not Available.

Carmel, Amos and Yaron, Arich "An Intramolecularly Quenched Fluorescent Tripeptide As A Fluorogenic Substrate of Angiotensin–I–Converting Enzyme and a Bacterial Dipeptidyl Carboxypeptidase." *Eur. J. Biochem.* 87, 265–273 (1978) Month not Available.

Fleminger, Gideon, et al. "Use of An Intramolecularly Quenched Fluorogenic Substrate For Study Of A Thiol–Dependent Acidic Dipeptidyl Carboxypeptidase In Cellular Extracts And In Living Cells." *FEBS Letters* 135, 131–134 (1981) Month not Available.

Sato, Eisuke et al. "Novel Fluorogenic Substrates Containing Bimane System For Microdetermination of Angiotensin I Converting Enzyme." *Chem. Pharm. Bull.* 37, 145–147 (1989) Month no Available.

Sato, Eisuke et al. "Bimane Fluorogenic Substrates For Microdetermination of Angiotensin Converting Enzyme Level In Serum." *Chem. Pharm. Bull.* 39, 2146–2148 (1991) Month not Available.

Matayoshi, Edmund D. et al. "Novel Fluorogenic Substrates for Assaying Retroviral Proteases by Resonance Energy Transfer." *Science* 247, 954–958 (1990) Month not Available.

Maggiora, Linda L. et al. "A General Method For The Preparation of Internally Quenched Fluorogenic Protease Substrates Using Solid–Phase Peptide Synthesis." *J. Med. Chem.* 35, 3727–3730 (1992) Month not Available.

*Primary Examiner*—Louise Leary
*Attorney, Agent, or Firm*—Campbell & Flores LLP

[57] ABSTRACT

Disclosed are new fluorogenic substrates for assay of angiotensin converting enzyme, a process for preparing them and methods for using them to assay angiotensin converting enzyme and to screen antihypertensive agents which inhibit angiotensin converting enzyme.

23 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Asp Arg Val Tyr Ile His Pro Phe His Leu
    1                5                              10

( 2 ) INFORMATION FOR SEQ ID NO:2:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:2:

Asp Arg Val Tyr Ile His Pro Phe
1               5

(2) INFORMATION FOR SEQ ID NO:3:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Binding-site
(B) LOCATION: 1
(D) OTHER INFORMATION: /note= "Xaa is E-Lk, wherein E is 5-[(2- aminoethyl)amino]napthalene-1-sulfonyl and Lk is a linking arm derived from a compound containing at least two functional groups condensable with amino groups."

(ix) FEATURE:
(A) NAME/KEY: Peptide
(B) LOCATION: 2
(D) OTHER INFORMATION: /note= "Xaa is a direct bond, or a residue of protein constituent amino acids or amino acid derivatives other than tryptophan."

(ix) FEATURE:
(A) NAME/KEY: Peptide
(B) LOCATION: 3
(D) OTHER INFORMATION: /note= "Xaa is a residue of protein constituent amino acids or amino acid derivatives other than tryptophan."

(ix) FEATURE:
(A) NAME/KEY: Peptide
(B) LOCATION: 4..5
(D) OTHER INFORMATION: /note= "Xaa is an independent residue of protein constituent amino acids or amino acid derivatives provided that at least one of these Xaa groups is a tryptophan residue."

(xi) SEQUENCE DESCRIPTION: SEQ ID NO:3:

Xaa Xaa Xaa Xaa Xaa
1               5

(2) INFORMATION FOR SEQ ID NO:4:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Xaa is a direct bond, or a residue of protein constituent amino acids or amino acid derivatives other than tryptophan."

(ix) FEATURE:
(A) NAME/KEY: Peptide
(B) LOCATION: 2
(D) OTHER INFORMATION: /note= "Xaa is a residue of protein constituent amino acids or amino acid derivatives other than tryptophan."

(ix) FEATURE:
(A) NAME/KEY: Peptide (B) LOCATION: 3..4
(D) OTHER INFORMATION: /note= "Xaa is an independent residue of protein constituent amino acids or amino acid derivatives provided that at least one of these Xaa groups is a tryptophan residue."

(xi) SEQUENCE DESCRIPTION: SEQ ID NO:4:

Xaa Xaa Xaa Xaa
1

FLUOROGENIC SUBSTRATES FOR ASSAY OF ANGIOTENSIN CONVERTING ENZYME

FIELD OF THE INVENTION

The invention relates to new fluorogenic substrates for assay of angiotensin converting enzyme, a process for preparing them and methods for using them to assay angiotensin converting enzyme and to screen the antihypertensive agents which inhibit angiotensin converting enzyme.

BACKGROUND OF THE INVENTION

Angiotensin converting enzyme (ACE) [EC 3.4.15.1] is a dipeptidyl carboxypeptidase, also known as a zinc-containing metalloprotease, which catalyzes the release of dipeptides from the carboxyl terminus of oligopeptides [1]. Its best known physiological function is the physiological reaction involved in Renin-Angiotensin-System (RAS). The enzyme converts the physiologically inactive decapeptide angiotensin I to the octapeptide angiotensin II. The catalytic hydrolysis reaction can be expressed as follows:

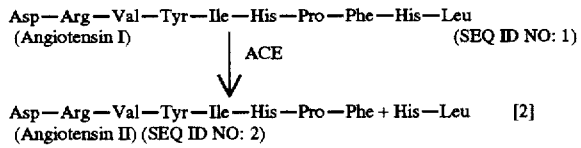

Asp—Arg—Val—Tyr—Ile—His—Pro—Phe—His—Leu
(Angiotensin I) (SEQ ID NO: 1)

Asp—Arg—Val—Tyr—Ile—His—Pro—Phe + His—Leu    [2]
(Angiotensin II) (SEQ ID NO: 2)

Angiotensin II is the most important function effector in RAS. It induces a variety of physiological reactions, including the contraction of blood vessels and the stimulation of aldosterone released by adrenal cortex resulting in the retention of sodium and the increase of blood pressure. Therefore, it is closely related to the formation of hypertension [3,4].

The drugs currently suggested for use to treat hypertension can be classified into four groups: (1) calcium ion antagonists, (2) ACE inhibitors, (3) diuretics and (4) β-sympathetic inhibitors. Among them, ACE inhibitors capable of inhibiting the conversion of angiotensin i to angiotensin II catalyzed by ACE thereby preventing the increase of blood pressure are good antihypertensive agents [5]. A simple and sensitive method for assay of ACE activity is an essential tool for developing antihypertensive agents which inhibit angiotensin converting enzyme.

One of the most commonly used methods for assay of ACE activity is to measure the rate of release of hippurate from hippuryl-histidyl-leucine substrate catalyzed by ACE. The hippurate is separated from unhydrolyzed substrate and is quantified by measuring its absorbance at 228 nm [6,7].

Another similar substrate for assay of ACE activity is hippurylglycylglycine. When the substrate is used for assaying ACE activity, the glycylglycine released after catalytic cleavage by ACE is measured by a quantitative ninhydrin reaction [8].

The above methods are relatively time-consuming and impractical for screening and characterizing a vast number of antihypertensive agents.

A fluorophone is a compound which excites at one wavelength and emits at another wavelength. Such compound can be used in enzyme assay. For example, in the above method for assay of ACE activity using hippuryl-histidyl-leucine as substrate, the released histidyl-leucine dipeptide can also be fluorometrically measured after the reaction with o-phthalaldehyde (OPA) [9,10] or fluorescamine [11] [12].

In another fluorometric assay, the activity of hydrolytic enzyme is measured on the basis of the change in fluorescence intensities of intramolecularly quenched fluorogenic substrate [13]. The mechanism is different from the above mentioned fluorometric assay and concerns with resonance energy transfer.

Resonance energy transfer, also known as non-radioactive energy transfer, is a mechanism in which an excited fluorophore, the donor, transfers its excitation energy to another fluorophore, the acceptor, situated within a suitable distance in the same system [13,14]. Generally, the emission spectrum of the donor overlaps the excitation spectrum of the acceptor. Resonance energy transfer is not mediated by direct contact of molecules. When energy transfer occurs in a system, the fluorescence intensity significantly decreases if the system is excited at the wavelength of excitation peak of the donor and detected at the wavelength of emission peak. The phenomenon is called quenching [14].

The efficiency of resonance energy transfer is expressed by the following equation [15]:

$$e = 1 - \frac{F}{F_o} = \frac{r_0^6}{r^6 + r_o^6}$$

wherein

F and $F_o$ are the fluorescence intensities of the donor in the presence or absence of the acceptor, respectively;

r is the distance between the centers of the donor and in the presence or absence of the acceptor, respectively;

r is the distance between the centers of the donor and the acceptor; and $r_o$ is the distance between the donor and the acceptor when the transfer efficiency is 50%.

As shown in the above equation, the energy transfer efficiency depends on the spectral overlap between the emission spectrum of the donor and the absorption spectrum of the acceptor and the distance between the two fluorophores. It has been experimentally verified that an energy donor-acceptor pair can be used to reveal the proximity between two fluorophores.

"Intramolecularly quenched fluorogenic substrate" is a molecule wherein an energy transfer donor—acceptor pair exists and the fluorogenic property of the donor quenches. The substrate contains an enzymatically cleavable bond situated between the donor and the acceptor. When the bond is cleaved by an enzyme, fluorescence is released as the result of canceling the quenching interaction between the donor and the acceptor [13]. Such molecule has been utilized to assay the activity of proteolytic enzymes.

Intramolecularly quenched fluorogenic peptides known to be useful for assay of ACE activity include p-nitrobenzyloxycarbonylglycyl-L-tryptophyl-glycine [16], o-aminobenzoyl-glycyl-p-nitro-L-phenylalanyl-L-proline [17], dansyl-glycyl-p-nitro-L-phenylalanine [18] and bimane (1,7-dioxo-2,3,5,6-tetramethyl-1H, 7H-pyrazolo-[1, 2-a]pyrazole) [19,20]. Owing to the hydrophobic characteristic, bimane substrates have a solubility problem and need to be dissolved in organic solvents. Dimethyl sulfoxide (DMSO) is the most commonly used organic solvent for bimane [9,20]. Although the amount of DMSO added in the assay mixture is low, it apparently deactivates ACE and consequently influences the accuracy of assay.

Furthermore, 5-[(2-aminoethyl)amino]naphthalene-1-sulfonic acid (EDANS) and 4-(4-dimethylaminophenylazo) benzoic acid (DABCYL) are broadly applied to the quenched fluorogenic substrates of endopeptidases, such as HIV-1 protease [21], HAV-3C protease and renin [22]. These substrates consist of peptides with a fluorescent donor, EDANS, and a quenching acceptor, DABCYL, attached to

3 the carboxyl- and amino-termini, respectively. These substrates are very suitable for the assay of endopeptidases but not appropriate for the assay of exopeptidases.

SUMMARY OF THE INVENTION

An object of the invention is to provide new fluorogenic substrates for assay of ACE activity which possess excellent enzymatic kinetic properties.

An other object of the invention is to provide a process for the preparation of the new fluorogenic substrates.

A further object of the invention is to provide a simple and sensitive method for assay of ACE activity using the new fluorogenic substrates.

Yet another object of the invention is to provide a method for rapidly and accurately screening the antihypertensive agents which inhibit ACE activity.

These and other objects, advantages and features of the invention will be more fully understood and appreciated by reference to the written specification.

DETAILED DESCRIPTION OF THE INVENTION

Figure 1:
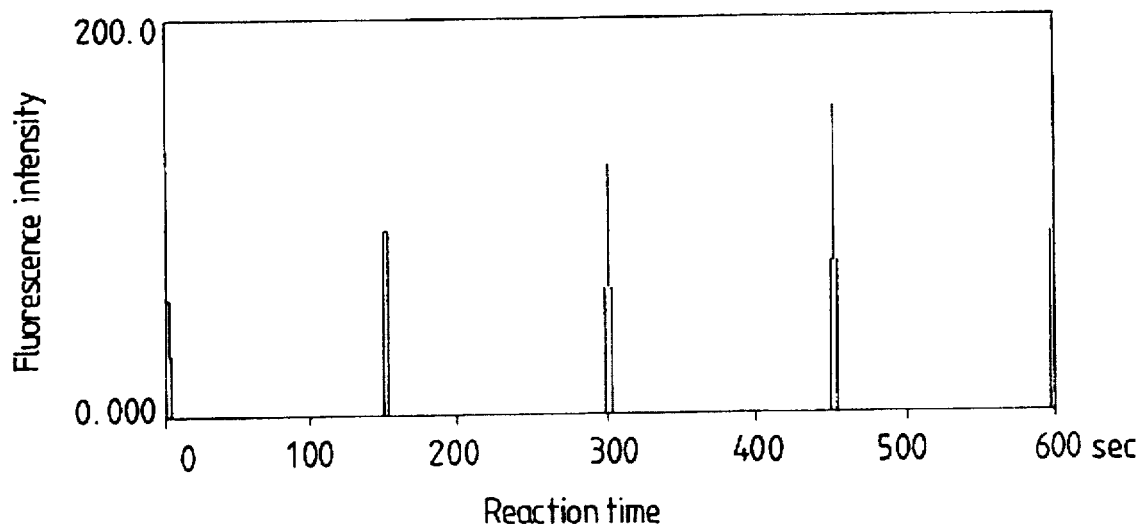
FIG. 1 is a diagram showing the hydrolysis of ES-FWF by ACE as monitored by fluorescence spectrophotometer.

It is found in the subject invention that EDANS and tryptophan are a good fluorescent donor-acceptor pair and can be used to design intramolecularly quenched fluorogenic substrates.

Accordingly, the subject invention provides fluorogenic substrate of the following formula:

E-Lk-AA$_1$-AA$_2$-AA$_3$-AA$_4$ (SEQ ID NO: 3)

wherein E is 5-[(2-aminoethyl)amino]naphthalene-1-sulfonyl (abbreviated as EDANSYL);

Lk is a linking arm derived from a compound containing at least two functional groups condensable with amino groups;

AA$_1$ is a direct bond, or a residue of protein constituent amino acids or amino acid derivatives other than tryptophan;

AA$_2$ is a residue of protein constituent amino acids or amino acid derivatives other than tryptophan; and AA$_3$ and AA$_4$ are independently residues of protein constituent amino acids or amino acid derivatives provided that at least one of AA$_3$ and AA$_4$ is tryptophan residue.

EDANS, having the following structure

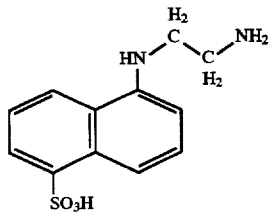

serves as the energy donor fluorophore in the new fluorogenic substrates of the invention.

In the new fluorogenic substrates of the invention, Lk represents a linking arm derived from a compound having at least two functional groups condensable with EDANS and with the amino acid residue of the peptide substrate, respectively.

4

The functional groups which can condense with —NH$_2$ group are well known in the art and comprise halogens such as fluorine, chlorine, bromine and iodine; acyl groups, such as those derived from mono-, di-, or poly- saturated and unsaturated aliphatic carboxylic acids; ester groups, such as those of mono-, di-, or poly- saturated and unsaturated aliphatic carboxylic acids; aldehyde groups; carboxyl groups, such as those derived from mono-, di-, or poly-saturated and unsaturated aliphatic carboxylic acids; and other similar functional groups. For example, Wong, S. S.(1991) Chemistry of Protein Conjugation and Cross-Linking, CRC Press, Inc. [23] discloses a variety of functional groups which can condense with amino groups. The literature is incorporated herein by reference in its entirety. The at least two functional groups of the compound may be the same or different, as long as they can condense with the amino groups in EDANS and in amino acid, respectively. Therefore, the linking arm of the subject invention is derived from the compounds having at least two functional groups which are the same or different and selected from the group consisting of halogens, acyl groups, ester groups, aldehyde groups, carboxyl groups and derivatives thereof.

The compounds suitable for use in the invention having at least two functional groups condensable with amino groups comprise alkanes which are di- or poly-substituted by the same halo atoms, such as 1,2-dichloroethane, 1,2-dibromoethane, 1,2-diiodoethane, 1,3-dichloropropane, 1,3-dibromopropane, 1,3-diiodopropane, 1,2,3-trichloropropane, 1,2,3-tribromopropane, 1,2,3-triiodopropane, 1,4-dichlorobutane, 1,4-dibromobutane, 1,4-diiodobutane, 1,2,4-trichlorobutane, 1,2,4-tribromobutane, 1,2,4-triiodobutane, 1,5-dichloropentane, 1,5-dibromopentane, 1,5-diiodopentane, 1,6-dichloropentane, 1,6-dibromopentane, 1,6-dibromopentane and suitable derivatives of haloalkanes; acyl di- or polyhalides, such as oxalyl dichloride, malonyl dichloride, succinyl dichloride, glutaryl dichloride, adipic dichloride, maleoyl dichloride, fumaryl dichloride, tartaryl dichloride, citric dichloride and suitable derivatives of acyl halides; carboxylic di- or poly- esters, such as dialkyl ester of oxalic acid, malonic acid, succinic acid, glutaric acid, adipic acid, maleic acid, fumaric acid, tartaric acid or citric acid, for example, dimethyl ester, diethyl ester, dipropyl ester, dibutyl ester and esters, or trimethyl ester, triethyl ester, tripropyl ester, tributyl ester and suitable derivatives of esters, or bis-N-hydroxysuccinimidyl esters, bis-nitrophenyl esters or bis-imidoesters, and suitable derivatives of esters; acid anhydrides, such as oxalic anhydride, malonic anhydride, succinic anhydride, glutaric anhydride, adipic anhydride and suitable derivatives of acid anhydrides; dialdehydes, such as oxalic aldehyde, malonic aldehyde, succinic aldehyde, glutaric dialdehyde, adipic aldehyde and the like; di- or polycarboxylic acids, such as oxalic acid, malonic acid, succinic acid, glutaric acid, adipic acid, maleic acid, fumaric acid, tartaric acid or citric acid and suitable derivatives of carboxylic acids; and similar compounds.

The compounds having at least two different functional groups condensable with amino groups comprise alkanes which are di- or poly- substituted by different halogens, such as 1-bromo-2-chloroethane, 1-bromo-3-chloropropane and suitable derivatized compounds; aldehydic acids, such as malonaldehydic acid, succinaldehydic acid, glutaraldehydic acid and adipaldehydic acid; monoester of di- or polycarboxylic acids and di- or polyesters of poly- carboxylic acids, such as oxalic acid, malonic acid, succinic acid, glutaric acid, adipic acid, maleic acid, fumaric acid, tartaric acid or citric acid monoester and citric acid diester; and di- or poly- carboxylic acid monohalides or polycarboxylic acid dihalides, such as oxalic, malonic, succinic, glutaric, adipic, maleic, fumaric, tartaric or citric monochloride and citric dichloride; and suitable derivatized compounds.

Preferably, the linking arm of the new fluorogenic substrate is derived from the compounds which have the same functional groups and are selected from dihaloalkanes, dicarboxylic halides, dicarboxylic alkyl esters, or bis-N-hydroxysuccinimidyl esters, bis-nitrophenyl esters or bis-imidoesters, di-carboxylic acids or acid anhydrides. More preferably, the linking arm is derived from acid anhydrides, especially succinic anhydride.

Therefore, in one embodiment of the invention, EDANS and oligopeptide molecules are linked by succinic linking arm.

The novel fluorogenic substrate of the invention is a modified oligopeptidyl substrate which may be a modified tripeptidyl molecule having three amino acid residues or a modified tetrapeptidyl molecule having four amino acid residues. When the fluorogenic substrate of the invention is a modified tripeptidyl molecule, $AA_1$ is a direct bond. When the fluorogenic substrate of the invention is a modified tetrapeptidyl molecule, $AA_1$ and $AA_2$ may be the same or different and independently represents any amino acid residue which is not fluorogenic, namely, the residue of any protein constituent amino acids or amino acid derivatives other than tryptophan.

In the new fluorogenic substrate of the invention, tryptophan serves as the energy acceptor fluorophore. As stated above, ACE catalyzes the hydrolysis of oligopeptides to release dipeptides from C-terminus. Therefore, at least one of the two amino acid residues at the C-terminus of the new oligopeptide fluorogenic substrates is tryptophan residue. That is, at least one of $AA_3$ and $AA_4$ is tryptophan residue and the other is the residue of any protein constituent amino acids or amino acid derivatives.

The term "protein constituent amino acids" used herein comprises the amino acids naturally existing in protein, including arginine, histidine, leucine, isoleucine, lysine, hydroxylysine, methionine, phenylalanine, tyrosine, valine, alanine, aspartic acid, asparagine, cysteine, glutamic acid, glutamine, glycine, proline, 4-hydroxyproline, serine, threonine and tryptophan. The term "amino acid derivatives" used herein includes such as ($N^\epsilon$-t-Boc)-lysine, D-alanine, D-glutamic acid, norvaline, 4-(E)-butenyl-4(R)-methyl-N-methyl-L-threonine, N-methylleucine (MeLeu), aminoisobutyric acid (α-methylalanine, Aib) or 3-(S)-hydroxy-4-(S)-amino-6-methyl heptoic acid (Sta).

Preferably, in case $AA_1$ is not a direct bond, it is an amino acid residue which may be the same with or different from $AA_2$, and $AA_1$ and $AA_2$ are independently selected from phenylalanine, leucine, alanine, glycine, lysine and ($N^\epsilon$-t-Boc)-lysine residues. One of $AA_3$ and $AA_4$ is tryptophan residue and the other is selected from tryptophan, histidine, phenylalanine, leucine, alanine, glycine, glutamic acid, arginine, proline, lysine and ($N^\epsilon$-t-Boc)-lysine residues.

Preferably, $AA_1$ is a direct bond and $AA^2$ is selected from phenylalanine, leucine, alanine, glycine, lysine and ($N^\epsilon$-t-Boc)-lysine residues. When $AA_3$ is tryptophan residue, $AA_4$ is selected from tryptophan, phenylalanine, leucine, glycine, lysine, histidine, alanine, glutamic acid, arginine and proline. When $AA_4$ is tryptophan, $AA_3$ is selected from tryptophan, histidine, phenylalanine, leucine, alanine, glycine, lysine and ($N^\epsilon$-t-Boc)-lysine residues.

More preferably, $AA_1$ is a direct bond, $AA_2$ is phenylalanine residue, one of $AA_3$ and $AA_4$ is tryptophan residue and the other is selected from tryptophan, phenylalanine, glycine, histidine, lysine and leucine residues. Particularly, when $AA_3$ is tryptophan residue, $AA_4$ is selected from tryptophan, phenylalanine, glycine, histidine, lysine and leucine; when $AA_4$ is tryptophan residue, $AA_3$ is selected from tryptophan and histidine.

The most preferred substrate of the invention is a modified tripeptidyl molecule in which $AA_1$ is a direct bond, $AA_2$ is phenylalanine residue, $AA_3$ is tryptophan residue and $AA_4$ is phenylalanine residue.

The substrate of the invention can be prepared by any conventional processes. For example, the tripeptidyl or tetrapeptidyl molecule can first be prepared by solid phase peptide synthesis, followed by coupling one functional group of the linking arm with the α-amino group of the tri- or tetrapeptide and then by linking EDANS to the other functional group of the linking arm using peptide bond forming process.

For example, the preferred embodiment of the invention, EDANS-succinyl-peptide, can be prepared as follows:

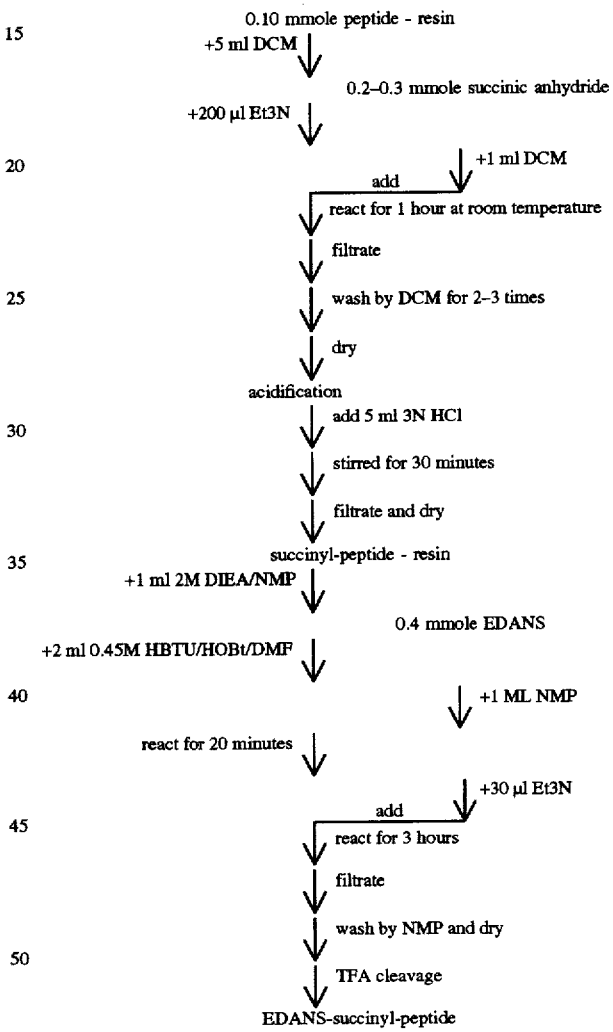

The definition of each abbreviation can be seen in the following text of the specification.

In the new fluorogenic substrates of the invention, EDANS group at the N-terminus transfers the absorbed energy to acceptor fluorophore, tryptophan residue, at the C-terminus. Therefore, in a complete fluorogenic substrate of the invention, the fluorogenic character is quenched. When the substrate of the invention is cleaved by ACE existing in a test system, the dipeptide at the C-terminus containing tryptophan residue acceptor will be released, and quenching will be cancelled simultaneously. Therefore, the new fluorogenic substrate of the invention can be used for assay of ACE activity.

It has been proved that the new fluorogenic substrate of the invention possesses excellent enzymatic kinetic properties. The kcat/Km value is comparable to or higher than that of the substrates conventionally used for assay of ACE activity. The new fluorogenic substrate detects ACE activity more rapidly and sensitively. Moreover, the new fluorogenic substrate of the invention has an excellent solubility in the range of 7–40 g/l of aqueous buffer and thus can directly be Used to test enzymatic kinetic characters without any organic solvent. This property overcomes the solubility difficulty of the prior art Bimane substrate that organic solvents adversely affecting ACE activity must be used. Therefore, another aspect of the invention provides a method for assay of ACE which comprises using the new fluorogenic substrate of the invention.

When the new fluorogenic substrate of the invention is used for assay of ACE activity, it can be diluted with a suitable buffer solution to a substrate solution of suitable concentration. For example, the substrate can be diluted with 50 mM Hepes buffer solution, pH 8.2, containing 0.2M NaCl and 0.6 M $Na_2SO_4$ to 15 µM substrate solution. Then, an aliquot of substrate solution (e.g., 0.5 ml or 1.0 ml) and sample (e.g. 20 µl ) are placed in quartz colorimetric tube, and a fluorospectrophotometer is used to test the change in florescence intensity at 5 or 6 time intervals.

Any fluorospectrophotometer can be used. The preferred meter is one with shutter function. For example, an activity test can be completed within 5 minutes if the light source is set to be turned on per minute, one second each time. If desired, one can also shorten the exposure intervals to shorten the time for assay. It has been proved that if the light source is turned on at a 15-second interval, the activity assay can be accurately completed within one minute.

The product concentration can be obtained from conversing the change in fluorescence intensity according to the following equation:

$$E = 132.8C - 2.7$$

where E is the fluorescence intensity obtained, and

C is the product concentration (µM).

The substrate variation in quantity per minute can be obtained from the slope of the regression equation based on the data of 5 or 6 points.

Moreover, as stated above, ACE inhibitor is an excellent antihypertensive agent. A simple and sensitive method for assay of ACE activity is an essential tool for developing the anti-hypertensive agents which inhibit angiotensin converting enzyme. As noted above, when the new fluorogenic substrate is used for assay of ACE activity, the activity assay of sample can be completed within five minutes. The fastest is within one minute.

Therefore, the subject invention further provides a method for rapidly and accurately screening the antihypertensive agents which inhibit angiotensin converting enzyme, said method being characterized by using the new fluorogenic substrate of the invention to assay the residual ACE activity after applying the antihypertensive agents to ACE solution.

The method of using the new fluorogenic substrate of the invention for screening the material with ACE inhibiting activity is similar to the method for assaying ACE activity stated above. The substrate can be diluted with suitable buffer solution (such as the 50 mM Hepes buffer solution stated above) to a substrate solution of appropriate concentration (for example, 15 µM.) A suitable amount (such as 0.5 ml) of substrate solution is mixed with an enzyme solution (such as 20 µl containing $2.6 \times 10^{-4}$ units) and sample diluted to suitable concentration (such as 100 µl) or equal amount of distilled water or buffer solution (as blank control). The change in fluorescence is fluorometrically determined. When the variation in fluorescence of a tested sample is lower than that of the control, it can be preliminarily deduced that the sample exhibits ACE inhibitory activity.

The sample to be tested or the sample which is preliminarily deduced as an ACE inhibitor can be directly diluted into 5 different concentrations and separately added to two groups of reaction solution containing different substrate concentrations. 10 groups of data can thus be obtained. The inverse of reaction rates are plotted against the sample concentrations. The cross-point of the two regression lines gives the Ki value. The inhibitory activity of the sample can thus be confirmed by the value.

The objects and efficacies of the invention can be further illustrated by the following non-limitative examples.

The meanings of the abbreviations in the specification and the example are as follows:

| | |
|---|---|
| HMP-resin | (4-hydroxymethylphenoxymethyl) resin |
| Fmoc | 9-fluorenylmethoxycarbonyl |
| TFA | trifluoroacetic acid |
| EDANS | 5-[(2-aminoethyl)amino)naphthalene-1-sulfonic acid |
| DCC | dicyclohexylcarbonyldiimine |
| DAMP | dimethylaminopyridine |
| DMF | N,N-dimethylformamide |
| NMP | N-methylpyrrolidone |
| DCM | dichloromethane |
| HOBt | 1-hydroxybenzotriazole |
| HBTU | 2-(1H-benzotriazol-1-yl)-1,1,3,3-tetramethyluronium hexafluorophosphate |
| DIEA | diisopropylethylamine |
| DMSO | dimethyl sulfoxide |
| ACE | angiotensin converting enzyme |
| Gly, G | glycine |
| Ala, A | alanine |
| Val, V | valine |
| Leu, L | leucine |
| Ile, I | isoleucine |
| Asp, D | Aspartic acid |
| Glu, E | glutamic acid |
| Arg, R | arginine |
| Lys, K | lysine |
| His, H | histidine |
| Phe, F | phenylalanine |
| Tyr, Y | tyrosine |
| Try, W | tryptophan |
| Pro, P | proline |
| ES | 5-[(2-aminoethyl)amino] naphthalene-1-sulfonyl-succinyl |
| Bim | 1,7-dioxo-2,3,5,6-tetramethyl-1H,7H-pyrazolo[1,2-a] pyrazole |
| Hip | hippuryl |
| Abz | o-aminobenzoyl |
| Dns | 1-dimethylaminonaphthylene-5-sulfonyl |
| FWF | phenylalanine-tryptophan-phenylalanine |
| FWG | phenylalanine-tryptophan-glycine |
| FWH | phenylalanine-tryptophan-histidine |
| FWK | phenylalanine-tryptophan-lysine |
| FWL | phenylalanine-tryptophan-leucine |
| FHW | phenylalanine-histidine-tryptophan |

EXAMPLES

Preparation of substrates ES-FWF, ES-FWG, ES-FWH, ES-FWK, ES-FWL and ES-FHW

The peptide substrates were synthesized using both automated and artificial procedures. Among the reagents used for peptide synthesis, HMP resin (0.92 mmol/gm.), Fmoc-L-Gly-OH, Fmoc-L-Leu-OH, Fmoc-L-Phe-OH, Fmoc-L-Trp-OH and Fmoc-L-His(Trt)-OH were purchased from Applied Biosystems (ABI, USA); Fmoc-Trp-p-alkoxybenzyl alcohol resin (0.76 meq/gm), Fmoc-His(Trt)-p-alkoxybenzyl alcohol resin (0.61 meq/gm) and Fmoc-Lys(Boc)-p-alkoxybenzyl alcohol resin (0.42 meq/gm) were obtained from Peninsula, USA; TFA and ethanedithiol were from Aldrich, USA; anisole and succinic anhydride were obtained from Merck, Germany; and EDANS was from Sigma, USA. First, the tripeptides with defined sequences were synthesized in a ABI synthesizer. Phe-Trp-Gly, Phe-Trp-Leu, Phe-Trp-Phe, Phe-Trp-His, Phe-Trp-Lys and Phe-His-Trp were assembled on the ABI Model 430A automated synthesizer. The standard coupling procedure [24] was performed using 0.25 mmol. The recommended conditions were followed. Briefly, peptides were synthesized on Fmoc-L-amino acid-p-alkoxybenzyl alcohol resins generating C-terminal ends or the HMP resin with which the first Fmoc-amino acid can be successfully coupled automatically onto the instrument. If automatic instrument loading is desired, 0.25 mmol of HMP resin is placed in the reaction vessel; 1 mmol of the desired Fmoc-amino acid is activated as the symmetric anhydride with DCC and subsequently coupled to the resin for approximately one hour. Because the HMP-resin has a hydroxyl group at its reactive site, 0.1M DMAP in DMF is added to catalyze the reaction. The Fmoc-group which protects the α-amino group of the amino acid is removed at the beginning of every cycle by a weak base (e.g. 20% piperidine).

In the standard reaction scale, 1.0 mmol of dry, protected amino acid contained in a cartridge was dissolved in a solution composed of 1.2 ml of NMP, 0.4–0.8 ml of DCM and 1 ml of 1M HOBt in NMP. The solution was transferred to the activator vessel followed by adding 1 ml of 1M DCC in NMP. After approximately 50 minutes of activation, the HOBt active ester was transferred to the reaction vessel. The activated Fmoc-amino acid reacts with the amino-terminus of the growing peptide chain to form a peptide bond. The Model 430A utilized 4 equivalents of the activated amino acid per 1 equivalent of the growing peptide chain for the coupling reaction. The time of one complete cycle was standardized as 92 minutes. After synthesis, the peptide-resin was deprotected by piperidine, then washed by NMP and DCM [24].

Post-synthesis Step

The standard synthesis procedure was performed using 0.10 mmol. After carefully washing (3×5 ml NMP and 3×5 ml DCM), the resin was suspended in 5 ml of DCM and 200 μl triethylamine. Succinic anhydride (0.2–0.3 mmol) which was dissolved in DCM was added. After one-hour reaction, the resin was filtrated, washed by DCM and dried under vacuum. The "blocked"-peptide resin was acidified by 5 ml of 3N HCl for 30 minutes. Then the EDANS group could be linked to the growing peptides using HBTU as activator to form peptide bond. HBTU was a new reagent for coupling amino acids with Fmoc/NMP chemistry. Activation with HBTU was much faster and more complete than carbodiimide-mediated reactions and resulted in shorter cycle times and increased coupling efficiency.

One mmol HBTU was dissolved in 2 ml of a solution of 0.5M HOBt and DMF. The acidified blocked-peptide resin which was dried under vacuum was swelling in this solution with additional NMP. DIEA was added to initiate activation. This activation proceeded 20 minutes. The coupling reaction was started by adding 0.4 mmol EDANS which was dissolved in NMP and triethylamine previously. Coupling time was 3 hours. After the synthesis, the peptide-resin was washed by NMP and DCM, then dried under vacuum overnight.

Final cleavage was performed in 10 ml of a solution of TFA: ethanedithiol: anisole (95: 1.25: 3.75) for 1.5 hours at room temperature. The solid support was filtered and washed with small amount of TFA cleavage solution. The filtrate was collected into 200 ml of cold ethyl ether to form precipitates which were collected with a 10–15 μM sintered glass filter and washed thoroughly with ethyl ether. The dry product was redissolved in 20% acetic acid, filtrated and lyophilized.

The crude peptides were purified by reversed-phase HPLC (Inertsil 50DS-2, 10.7×250 mm). Mobile phase A was 0.1% TFA in water and mobile phase B was 80% acetonitrile and 0.1% TFA. The gradient was 20% B to 90% B in 15 minutes, 90% B to 90% B from 15 to 17 minutes, and 90% B to 20% B from 17 to 19 minutes. The flow rate was 3 ml/min. Collected samples were then lyophilized and analyzed by JEOL JMS-HX 110 FAB-MS (fast atom bombardment mass spectrometer).

The solubility of the prepared ES-FWF, ES-FWG, ES-FWH, ES-FWK, ES-FWL and ES-FHW are in the range of 7–40 g/l of aqueous buffer.

Fluorometric Assay

Fluorescence data were recorded on a HITACHI Model F2000 fluorescence spectrophotometer (Tokyo, Japan) set at wavelengths of 286 nm (excitation) and 360 nm (emission). The rates of enzymatic hydrolysis of the fluorogenic compounds ES-FWF, ES-FWG, ES-FWH, ES-FWK, ES-FWL and ES-FHW were monitored fluorospectrophotometrically as follows: A solution of ACE was prepared at $1.3 \times 10^{-2}$ units/ml (concentration of enzyme was estimated by using the Bio-Rad protein assay kit with bovine serum albumin as a standard). ACE (from rabbit lung, Sigma Chemical Co.) had a specific activity of 0.2 units/mg protein. Activity was assayed with hippuryl-L-histidyl-L-leucine as a substrate. One unit of enzyme activity is the amount required to catalyze the formation of 1.0 μmol of hippuric acid per minute (in 50 mM Hepes, pH 8.3, and 0.3M NaCl at 37° C.). For fluorescence measurement, 20 μl of enzyme solution was added to 0.5 ml substrate solution ($2 \times 10^{-6}$–$6.5 \times 10^{-5}$M) in 0.05M Hepes buffer, pH 8.2, containing 0.2M NaCl and 1M $Na_2SO_4$, placed in an optical cell. No increase of fluorescence was observed in the absence of enzyme. The increase in fluorescence (emission at 360 nm, excitation at 286 nm) with time, in the presence of the enzyme, was recorded continuously. Since the product (and perhaps the substrate as well) is subject to photodecomposition, the slit width of the excitation monochromator must not be too large. Alternatively, the reaction can be monitored automatically by pulse illumination with a time interval of 150, sec, as shown in FIG. 1.

Dependence of the rate of hydrolysis on substrate concentration was established by initial rate measurements (within the first 10% of hydrolysis). The slope of the line was translated into molar concentrations of the released dipeptides using a calibration curve constructed by fluorescence measurements of solutions containing authentic dipeptide under identical conditions. Km values were calculated by the method of Lineweaver-Burk plots. Five points with approximately equidistance on the 1/[S] abscissa were obtained from the average of two independent measurements. Kinetic parameters for other substrates were also obtained by similar procedures.

Kinetic parameters of ES-FWF, ES-FWG, ES-FWH, ES-FWK, ES-FWL and ES-FHW for ACE were obtained by continuous spectrofluorometric assay, and the results are listed in Table I. In order to compare the characteristics of the ES-peptides with those of previously reported fluorogenic substrates, the kinetic parameters from literatures were collected for comparison.

TABLE I

| Substrate | $K_M$ (M) | $k_{cat}$ ($s^{-1}$) | $k_{cat}/K_m$ ($M^{-1}s^{-1}$) | Ref. |
|---|---|---|---|---|
| 1. ES-FWF | $4.5 \times 10^{-6}$ | 2.1 | $4.6 \times 10^5$ | This invention |
| 2. ES-FWG | $2.3 \times 10^{-5}$ | 2.0 | $8.9 \times 10^4$ | This invention |
| 3. ES-FWH | $4.9 \times 10^{-6}$ | 0.8 | $1.7 \times 10^5$ | This invention |
| 4. ES-FWK | $2.4 \times 10^{-5}$ | 3.8 | $1.6 \times 10^5$ | This invention |
| 5. ES-FWL | $2.7 \times 10^{-6}$ | 0.9 | $3.2 \times 10^5$ | This invention |
| 6. ES-FHW | $1.5 \times 10^{-5}$ | 2.0 | $1.3 \times 10^5$ | This invention |
| 7. Bim-GWL | $1.7 \times 10^{-4}$ | 1.2 | $7.0 \times 10^3$ | [19] |

TABLE I-continued

| Stubstrate | KM (M) | kcat (s⁻¹) | kcat/Km (M⁻¹S⁻¹) | Ref. |
|---|---|---|---|---|
| 8. Bim-FWL | $5.9 \times 10^{-5}$ | 3.1 | $5.2 \times 10^4$ | [19] |
| 9. Bim-FWP | $2.9 \times 10^{-5}$ | 2.5 | $8.7 \times 10^4$ | [19] |
| 10. Bim-FF(NO$_2$)P | $1.7 \times 10^{-5}$ | 5.1 | $3.0 \times 10^5$ | [20] |
| 11. Bim-FW(NO$_2$)P | $1.9 \times 10^{-5}$ | 5.4 | $2.9 \times 10^5$ | [20] |
| 12. Bim-FWP | $2.6 \times 10^{-5}$ | 6.9 | $2.6 \times 10^5$ | [20] |
| 13. Z(NO$_2$)-GWG | $9.0 \times 10^{-4}$ | | | [16] |
| 14. Abz-GF(NO$_2$)P | $1.9 \times 10^{-4}$ | 1.5 | $7.7 \times 10^3$ | [17] |
| 15. Dns-GF(NO$_2$)P | $4.2 \times 10^{-4}$ | 4.1 | $9.6 \times 10^3$ | [18] |

The Km values listed in Table I represent the affinity between the enzyme and the substrates. The lower the Km value, the higher the affinity of the enzyme to the substrate. Kcat values represent the largest number of substrate molecules which are converted into products at each active site per unit time. When the enzyme is saturated by a substrate, kcat value represents the catalytic efficiency of the enzyme.

As shown in Table I, the kcat/Km values of the fluorogenic substrates of the invention are comparable to or higher than those of the conventional substrates and thus the fluorogenic substrates of the invention are excellent fluorogenic substrates for assay of ACE activity. Although some conventional substrates exhibit kcat/Km values comparable to those of the invention (Substrates 10–12), they have the hydrophobic Bimane moiety in structure and consequently a low solubility.

Screening of ACE Inhibitor

Figure 2:
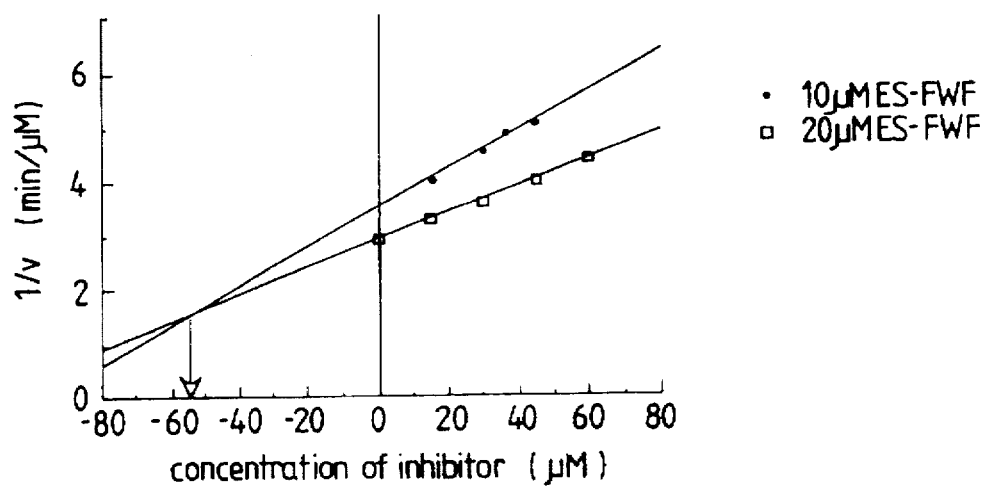
FIG. 2 is a diagram showing the screening of ACE inhibitor with ES-FWF.

Two groups of ES-FWF were diluted with 50 mH Hepes buffer to 20 μM and 10 μM substrate solutions, respectively. An ACE inhibitor was added. The resultant 20 μM ES-FWF substrate solutions contain 0, 15, 30, 45 and 60 μM inhibitor, respectively, and the resultant 10 μM ES-FWF substrate solutions contain 0, 15, 30, 36 and 45 μM inhibitor, respectively. 0.5 ml ES-FWF substrate reaction solutions of different concentrations were put into a colorimetric tube. The spectrophotometer was set at ex286 and em360. 20 μl ACE was added to initiate the reaction. After the reaction, fluorescence changes were recorded per second. The data obtained were converted into the fluorescence change per minute and by way of the equation E=132.8C-2.7, into the product quantity change per minute. The results are shown in FIG. 2. As shown in the figure, Ki=53.59 μM.

References

1. Skeggs, L. T., Marsh, W. H., Kahn, J. R., & Shumway, N. P. (1954) J. Exp. Med. 99, 275–282
2. Johnston, C. I. (1990) Drugs 39 (Suppl. 1), 21–31.
3. Ehlers, M. R. W. & Riordan, J. F. (1989) Biochemistry 28, 5311–5317.
4. Beneteau-Burnat, B. & Baudin, B. (1991) Critical Reviews in Clinical Laboratory Sciences 28, 337–356.
5. Lu, (1989) Chemical Industry Information, 9, 1–16.
6. Cushman, D. W. & Cheung, H. S. (1971) Biochem. Pharmacol, 20, 1637–1648.
7. Ryan, J. W., Chung, A., Ammons, C. & Carlton, M. L. (1977) Biochem. J. 167, 501–504.
8. Dorer, F. E., Kahn, J. R., Lentz, K. E., Levine, M. & Skeggs, L. T. (1976) Biochim. Biophys. Acta 429, 220–228.
9. Piquilloud Y. Reinharz A. & Roth M. (1970) Biochim. Biophys. Acta 206, 136–142.
10. Friehand J. & Silverstein E. (1976) Am. J. Clin. Pathol. 66, 416–424.
11. Conroy J. M., Lai C. Y. (1978) Anal. Biochem. 87, 556–561.
12. Kwarts, E., Beukenvekd, G., & Gazendam, Jr. (1982) Ann. Clin. Biochem. 19, 227–232.
13. Yaron, A., Carmel, A., & Katchalski-Katzir, E. (1979) Anal. Biochem. 95, 228–235.
14. David Freifelder, Physical. Biochemistry 2nd ed. pp537–556.
15. Forster, T. (1948) Ann. Physik. 2, 55–75.
16. Persson, A., & Wilson, I. B. (1977) Anal. Biochem. 83, 296–303.
17. Carmel, A. & Yaron, A. (1978) Eur. J. Biochem. 87, 265–273.
18. Fleminger, G., Goldenberg, D., & Yaron, A. (1981) FEBS Lett. 135, 131–134.
19. Sato, E., Nishikawa, S., & Kanaoka, Y. (1989) Chem. Pharm. Bull. 37, 145–147.
20. Sato, E., Hattori, H., Nishikawa, S., & Kanaoka, Y. (1991) Chem. Pharm. Bull. 39, 2146–2148.
21. Matayoshi, E. D., Wang, G. T., Krafft, G. A. & Erickson, J. (1990) Science 247, 954–958.
22. Maggiora, L. L., Smith, C. W., & Zhang, Z. A. A general Method for the synthesis of fluorogenic protease substrates using solid-phase peptide methods.
23. Wong, So S. (1991) Chemistry of Protein Conjugation and Cross-Linking. CRC Press, Inc.
24. Model 430A peptide synthesizer manual, 6-109-6-188.

We claim:

1. A fluorogenic substrate of the following formula:

E-Lk-AA$_1$-AA$_2$-AA$_3$-AA$_4$ (SEQ ID NO: 3)

wherein

E is 5-[(2-aminoethyl)amino]naphthalene-1-sulfonyl;

Lk is a linking arm derived from a compound containing at least two functional groups condensable with amino groups, AA$_1$ is a direct bond, or a residue of any protein constituent amino acids or amino acid derivatives other than tryptophan, AA$_2$ is a residue of any protein constituent amino acids or amino acid derivatives other than tryptophan, AA$_3$ and AA$_4$ are independently residues of any protein constituent amino acids or amino acid derivatives, provided that at least one of AA$_3$ and AA$_4$ is tryptophan residue.

2. The fluorogenic substrate according to claim 1, wherein the linking arm is derived from a compound having at least two functional groups independently selected from the group consisting of halogens, acyl groups, ester groups, aldehyde groups, carboxyl groups and suitable derivatives thereof.

3. The fluorogenic substrate according to claim 2, wherein the compound is selected from the group consisting of haloalkanes, acyl halides, aldehydes, aldehydic acids, carboxylic acids, carboxylic esters, carboxylic acid anhydrides and suitable derivatives thereof.

4. The fluorogenic substrate according to claim 3, wherein the compound is a carboxylic acid anhydride.

5. The fluorogenic substrate according to claim 4, wherein the carboxylic acid anhydride is succinic anhydride.

6. The fluorogenic substrate according to claim 1, wherein AA$_1$ and AA$_2$ are independently selected from the group consisting of phenylalanine, leucine, alanine, glycine, lysine and (N$^\epsilon$-t-Boc)-lysine residues.

7. The fluorogenic substrate according to claim 1, wherein AA$_1$ is a direct bond.

8. The fluorogenic substrate according to claim 6 or 7, wherein AA$_2$ is phenylalanine residue.

9. The fluorogenic substrate according to claim 1, wherein AA$_3$ and AA$_4$ are independently selected from the group consisting of tryptophan, histidine, phenylalanine, leucine, alanine, glycine, glutamic acid, arginine, proline, lysine and (N$^\epsilon$-t-Boc)-lysine residues.

10. The fluorogenic substrate according to claim 9, wherein AA$_3$ is tryptophan residue and AA$_4$ is selected from the group consisting of tryptophan, phenylalanine, leucine, glycine, lysine, histidine, alanine, glutamic acid, arginine and proline residues.

11. The fluorogenic substrate according to claim 9, wherein AA$_4$ is tryptophan and AA$_3$ is selected from the group consisting of tryptophan, histidine, phenylalanine, leucine, alanine, glycine, lysine and (N$^\epsilon$-t-Boc)-lysine residues.

12. The fluorogenic substrate according to claim 10, wherein AA$_4$ is selected from the group consisting of phenylalanine, leucine, glycine, lysine and histidine residues.

13. The fluorogenic substrate according to claim 11, wherein AA$_3$ is histidine residue.

14. The fluorogenic substrate according to claim 1, wherein Lk is succinyl, AA$_1$ is a direct bond, AA$_2$ is phenylalanine residue, AA3 is tryptophan or histidine residue, and AA$_4$ is tryptophan, phenylalanine, leucine, glycine, lysine or histidine residue.

15. The fluorogenic substrate according to claim 14, wherein AA$_3$ is tryptophan residue and AA$_4$ is phenylalanine residue.

16. A process for preparing the fluorogenic substrate of claim 1 comprising:

(1) preparing a peptide of the following formula

AA$_1$-AA$_2$-AA$_3$-AA$_4$ (SEQ ID NO: 4)

where AA$_1$ to AA$_4$ have the same meanings as defined in claim 1; and (2) linking the peptide and 5-[(2-aminoethyl)amino] naphthalene-1-sulfonic acid with a compound containing at least two functional groups condensable with amino groups.

17. The process according to claim 16, wherein the peptide AA$_1$-AA$_2$-AA$_3$-AA$_4$ (SEQ ID NO: 4) is prepared by solid phase peptide synthesis.

18. The process according to claim 16, wherein the compound containing at least two functional groups condensable with amino groups has at least two functional groups independently selected from the group consisting of halogens, acyl groups, ester groups, aldehyde groups, carboxyl groups and suitable derivatives thereof.

19. The process according to claim 18, wherein the compound is selected from the group consisting of haloalkanes, acyl halides, aldehydes, aldehydic acids, carboxylic acids, carboxylic esters, carboxylic acid anhydrides and suitable derivatives thereof.

20. The process according to claim 19, wherein the compound is carboxylic acid anhydride.

21. The process according to claim 20, wherein the carboxylic acid anhydride is succinic anhydride.

22. A method for assay of angiotensin converting enzyme comprising mixing a sample to be tested with the fluorogenic substrate according to claim 1, and determining the change in fluorescence intensity with a fluorospectrophotometer.

23. A method for screening the antihypertensive agents which inhibit angiotensin converting enzyme comprising mixing an agent to be tested with angiotensin converting enzyme and the fluorogenic substrate according to claim 1, and determining the change in fluorescence intensity with a fluorospectrophotometer.

* * * * *

UNITED STATES PATENT AND TRADEMARK OFFICE
CERTIFICATE OF CORRECTION

PATENT NO. : 5,723,307
DATED : March 3, 1998
INVENTOR(S) : Tsai et al.

It is certified that error appears in the above-identified patent and that said Letters Patent is hereby corrected as shown below:

Column 1,
Line 39, please delete "i to" and replace therefor with -- I to --.

Column 2,
Line 58, please delete "[9,20]." and replace therefor with -- [19,20]. --.

Column 3,
Line 34, please delete "provides" and replace therefor with -- provides a --.

Column 4,
Line 13, please add a carriage return after "entirety."

Column 5,
Line 53, please delete "AA$^2$" and replace therefor with -- AA$_2$ --.

Column 7,
Line 7, please delete "Used" and replace therefor with -- used --.

Column 9,
Line 59, please delete "with" and replace therefor with -- with a --.
Line 66, please delete "(Intertsil 50DS-2," and replace therefor with
-- (Intertsil 5 ODS-2, --.

Column 10,
Line 25, please insert a carriage before "For".

Signed and Sealed this

Thirtieth Day of April, 2002

*Attest:*

JAMES E. ROGAN
*Attesting Officer*    *Director of the United States Patent and Trademark Office*